United States Patent [19]

Morita et al.

[11] Patent Number: 6,117,864
[45] Date of Patent: *Sep. 12, 2000

[54] METHODS EMPLOYING STABLE PREPARATION CONTAINING AZELASTINE HYDROCHLORIDE

[75] Inventors: Yutaka Morita; Noritoshi Koyama; Shigemitsu Ohsawa, all of Honjo, Japan

[73] Assignee: ASTA Medica Aktiengesellschaft, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/889,807

[22] Filed: Jul. 8, 1997

Related U.S. Application Data

[63] Continuation of application No. 08/376,659, Jan. 20, 1995, abandoned, which is a continuation of application No. 08/092,998, Jul. 19, 1993, abandoned.

[30] Foreign Application Priority Data

Jul. 20, 1992 [JP] Japan .................................. 4-213243

[51] Int. Cl.$^7$ .................................................. A61K 31/55
[52] U.S. Cl. ............................................ 514/212; 514/947
[58] Field of Search ....................................... 514/212, 947

[56] References Cited

U.S. PATENT DOCUMENTS

| | | |
|---|---|---|
| 4,879,297 | 11/1989 | Mohjour et al. . |
| 5,059,427 | 10/1991 | Yoshida et al. . |
| 5,073,375 | 12/1991 | Yoshida et al. . |
| 5,110,814 | 5/1992 | Engel et al. . |
| 5,219,877 | 6/1993 | Shah et al. . |

FOREIGN PATENT DOCUMENTS

| | | |
|---|---|---|
| 0295411 | 3/1988 | European Pat. Off. . |
| 0368409 | 7/1989 | European Pat. Off. . |
| 0378086 | 3/1990 | European Pat. Off. . |
| 0428352 | 12/1990 | European Pat. Off. . |

OTHER PUBLICATIONS

Japanese Abstract JP–A–02 124 824 Week 9025 AN 90–189693 (1990).

Chemical Abstracts 113:120821s (1990).

*Primary Examiner*—Minna Moezie
*Attorney, Agent, or Firm*—Cushman Darby & Cushman IP Group of Pillsbury Madison & Sutro LLP

[57] ABSTRACT

Azelastine hydrochloride is combined certain fatty acids. The stability and absorbability of the composition is enhanced.

6 Claims, 3 Drawing Sheets

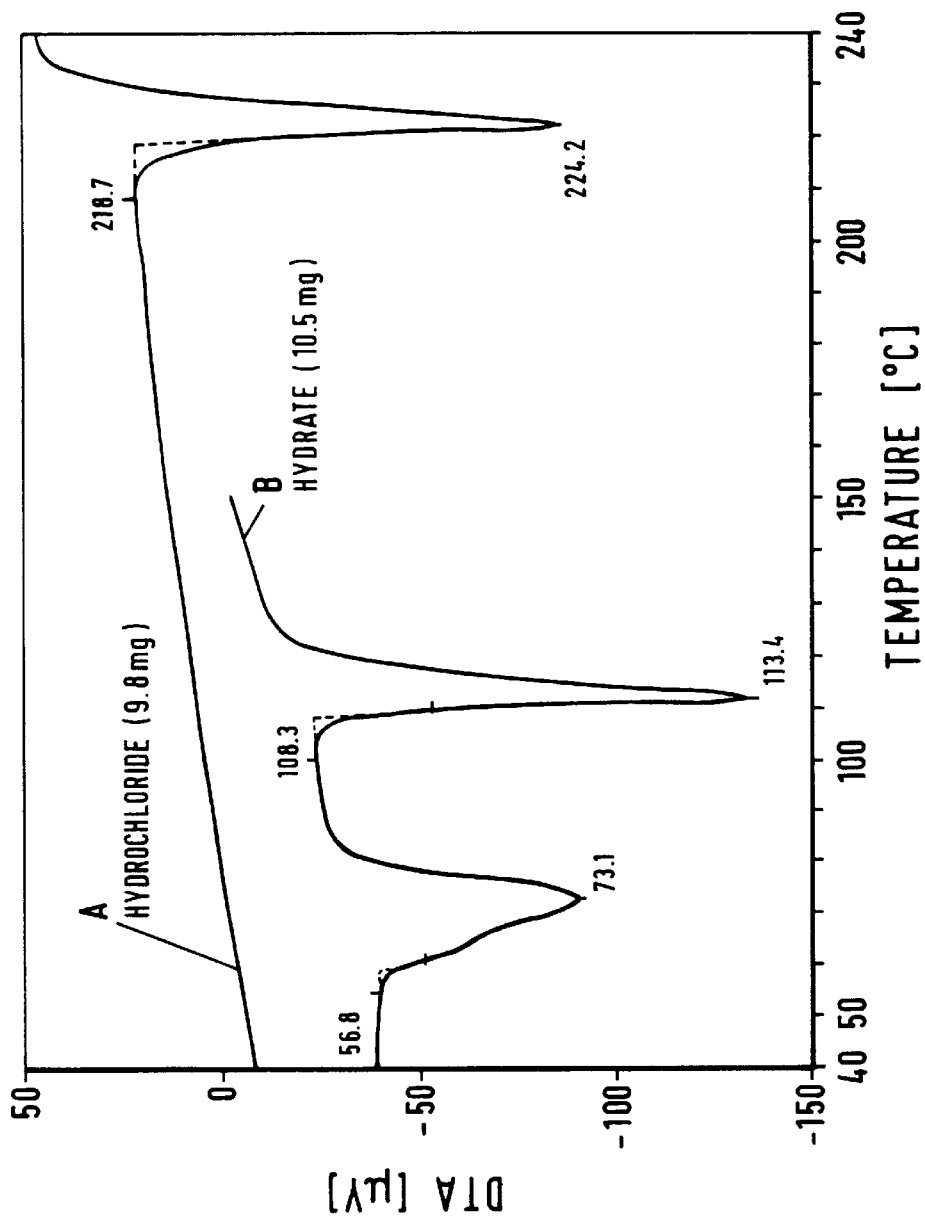

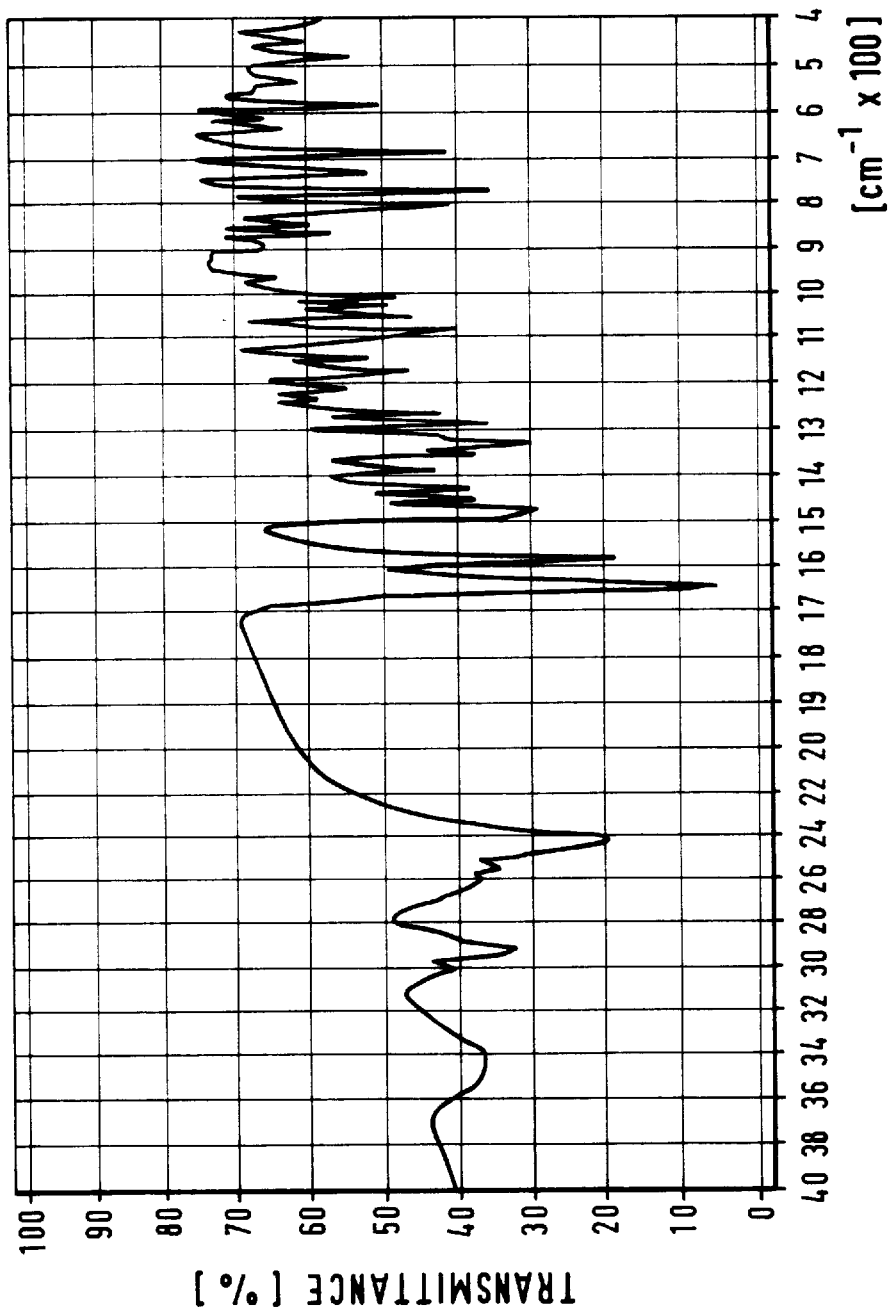
Fig. 2 IR SPECTRUM DIAGRAM FOR THE AZELASTINE HYDROCHLORIDE REFERENCE STANDARD

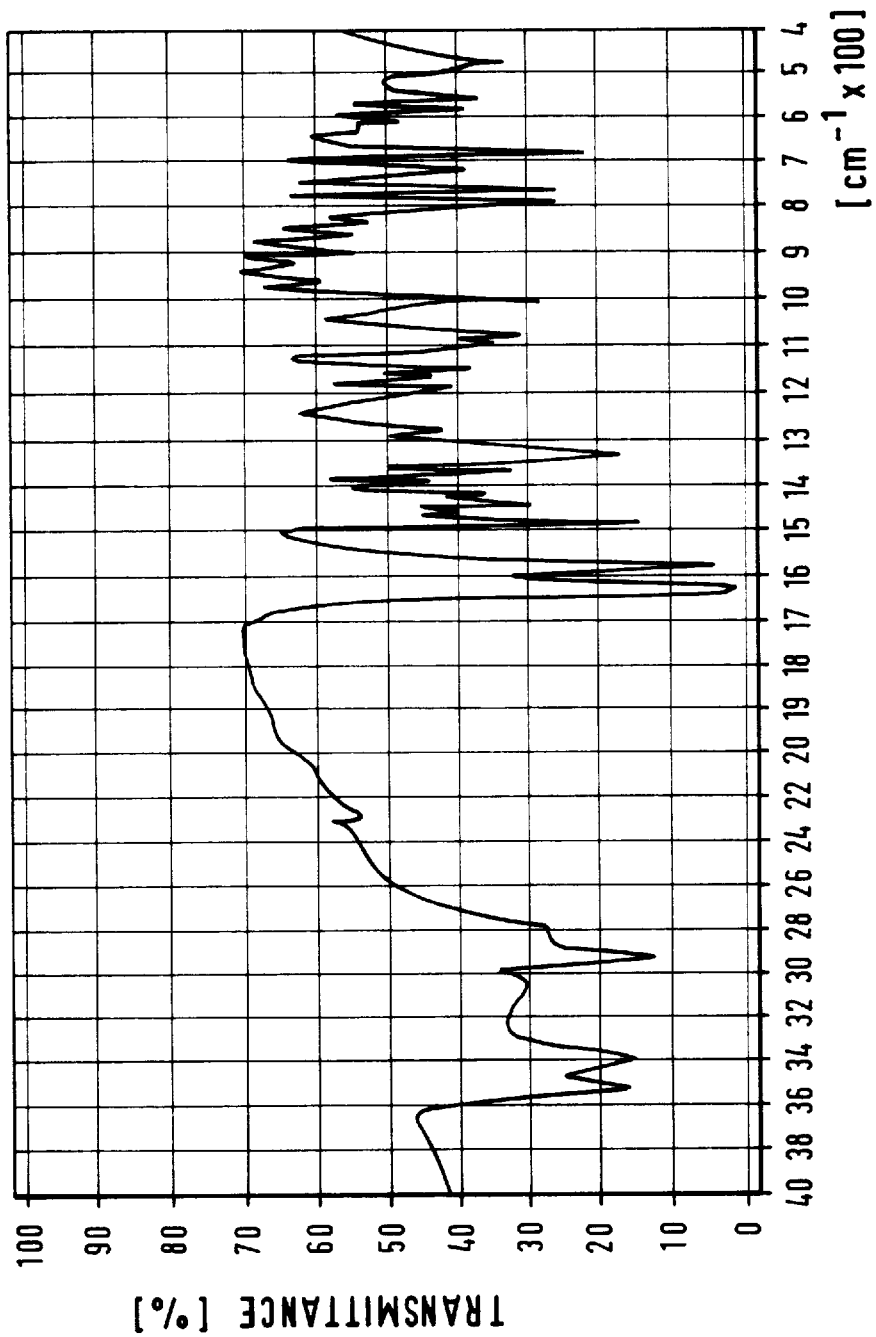

METHODS EMPLOYING STABLE PREPARATION CONTAINING AZELASTINE HYDROCHLORIDE

This is a continuation-in-part (CIP) of application Ser. No. 08/376,659, filed on Jan. 20, 1995, now abandoned which was a continuation application of 08/092,998 filed Jul. 19, 1993 (now abandoned).

The present invention relates to a stable preparation containing azelastine hydrochloride and a pharmaceutical composition incorporating it which has excellent percutaneous and mucosal absorbability.

BACKGROUND OF THE INVENTION

Azelastine hydrochloride has been used as an anti-allergy agent in medicinal treatments for bronchial asthma, allergic rhinitis, hives, eczema, dermatitis, atopic dermatitis, cutaneous pruritus, pruriqo, etc.

Generally, the absorption of basic medicines is thought to be high for non-dissociation types and low for dissociation types. For example, in Drug Metabolism Review 8(2), 223–233, 1978, it is shown that the percutaneous penetration speed of the basic medicine scopolamine is in direct proportion to the pH, and thus, since azelastine is a basic medicine, its absorption may also be expected to be favorable in direct proportion to the pH of the preparation. However, the acid dissociation constant (pKa) of azelastine is approximately 9.5. Thus, to make the proportion of non-dissociation type molecules 50%, it is necessary to adjust the pH of the preparation to 9.5, differing vastly from the physiological pH of the skin and membranes. Further, in an aqueous preparation, the non-dissociation type molecules of azelastine form crystalline hydrates of poor solubility. This causes precipitation, even if the pH and eventually the proportion of the non-dissociation type molecules is increased. Therefore, it is difficult to obtain a homogeneous preparation of azelastine.

In order to prevent precipitation of crystals in the preparation, previously known methods have included the step of adding solvents in which the crystals are readily soluble, or adding a surface active agent to solubilize the non-dissociation type medicine, or adding a water soluble polymer to suppress crystal growth.

Also, techniques of raising the percutaneous absorbability of azelastine hydrochloride have been reported in Japanese Patent publication (KOKAI) HEI 2-288827 and Japanese Patent Application SHO 63-278108. The former is characterized by the addition of an alkylglycerine to the preparation, and the latter is characterized by incorporation of a lactic acid ester of an aliphatic alcohol, such as, for example, cetyl lactate, myristyl lactate, lauryl lactate, and/or a fatty acid monoglyceride of 8 to 12 carbon atoms.

Further, in Japanese Patent publication (KOKAI) SHO 61-254532, a method is disclosed wherein a cationic water soluble medicine and an acidic oil soluble substance are combined to increase the percutaneous absorbability of the medicine. Another known general method for increasing the percutaneous and mucosal absorbability increases the amount of the main ingredient by maximizing its thermodynamic activity in the vehicle.

As described previously the producing of crystalline hydrate of azelastine gives rise to such an undesirable problem that the content of azelastine is heterogeneous, the absorbability of the medicine is lowered and the crystal thereof is changed into an undesirable form during administration.

Also, azelastine hydrochloride has a low solubility in solvents which may be used in pharmaceutical compositions, and thus precipitation of crystals cannot be prevented by addition of a solvent. In order to prevent the production of hydrates by addition of a surface active agent, it is necessary to use the surface active agent at a high concentration in the mixture, which can cause irritation of the skin or membrane. Further, it was not possible to suppress the production of hydrates of azelastine hydrochloride through the addition of a water soluble polymer. The alkyl glycerines disclosed in Japanese Patent publication (KOKAI) HEI 2-288827 are not commercially available and are difficult to obtain. Also in Japan there is as yet no example thereof as an external application and its safety has not been established. Thus, further research is necessary before it can come into actual use. With the technique disclosed in Japanese Patent publication (KOKAI) SHO 63-278108, when the amount of azelastine hydrochloride is high compared to the base, there is a marked improvement in the percutaneous absorbability thereof. On the other hand, when the amount is low, the azelastine hydrochloride disperses in the base, causing the disadvantage of poor percutaneous absorbability. Azelastine hydrochloride is a cationic drug, but no increase in absorbability was observed with the technique disclosed in Japanese Patent publication (KOKAI) SHO 61-254532. Also, if the amount of the drug in the vehicle is increased with consideration to the solubility of the drug in the vehicle, it is easy to increase the percutaneous absorbability. However, the many disadvantages in such a case include a rise in production cost, an increase in the danger of misuse of the preparation, and irritation of the skin due.

The inventors of the present invention carried out diligent research to overcome the above mentioned disadvantages, and succeeded in finding a solution through the method described below, by which the present invention was completed.

SUMMARY OF THE INVENTION

In accordance with the present invention, the foregoing difficulties are overcome by a pharmaceutical composition containing azelastine hydrochloride and a fatty acid of 8 or more carbon atoms. The invention also provides a pharmaceutical composition containing azelastine hydrochloride and a fatty acid of 8 or more carbon atoms, as well as 1, 2 or more ingredients selected from the group consisting of polyhydric alcohols, ethanol, isopropanol and lecithin.

The amount of azelastine hydrochloride is not limited, but an amount should be used which is necessary to cause the desired pharmacological effect, and that amount is between 0.001% and 2% by weight of the preparation. Amounts less than this will not provide an adequate pharmacological effect, and amounts greater than this are thought to be economically disadvantageous.

The fatty acid of 8 or more carbon atoms used according to the present invention may be a saturated, unsaturated, linear or branched aliphatic carboxylic acid. There is no particular restriction, but the preferred carbon number in the fatty acid is from 8 to 22. If the carbon number is lower than this, there is no effect of suppression of azelastine hydrate production, and fatty acids with higher carbon numbers are difficult to obtain as materials for medicinal preparations. The fatty acid should be relatively stable and change little through time, and it should cause little irritation and be highly safe when applied to the body. Preferred examples of fatty acids to achieve the object of the present invention include caprylic acid, capric acid, lauric acid, myristic acid, palmitic acid, stearic acid, isostearic acid, arachidic acid, behenic acid, palmitoleic acid, oleic acid, linolic acid, linolenic acid, linoleinic acid and erucic acid, etc. However, polyunsaturated fatty acids themselves have low stability. Thus, when making compositions containing them, it is necessary to preserve their stability by, for example, the addition of an antioxidant. More preferable fatty acids for incorporation in the preparation include capric acid, lauric acid, myristic acid, palmitic acid, stearic acid, isostearic acid, behenic acid, oleic acid, palmitoleic acid and linolic acid.

For stability of the preparation, and in order to achieve the effect of the present invention, the relative amount of fatty acid to azelastine hydrochloride should be more than 0.1 parts by weight of fatty acid, and preferably 0.3 to 10 parts by weight, and more preferably 0.5 to 5 parts by weight for each part of azelastine. If the amount of fatty acid is less than this, there is no effect of suppression of crystal formation of azelastine hydrate by adjustment of the pH. If the amount of fatty acid is greater than this range, then depending on the type of fatty acid selected and the other ingredients added to the preparation, there is sometimes precipitation of fatty acid salts or a mixture of a fatty acid and a fatty acid salt (fatty acid soap), called acid soap. This makes it difficult to obtain a stable, homogeneous preparation as desired by the present invention.

The polyhydric alcohols which may be used according to the present invention include propylene glycol, 1,3-butylene glycol, dipropylene glycol, sorbitol, maltitol, glycerine, etc. Ethanol, isopropanol and polyhydric alcohols may be used in amounts which uniformly dissolve the above mentioned fatty acid and azelastine hydrochloride, as well as lecithin. The amount of alcohol and/or polyhydric alcohol added is not particularly restricted, but should be 0.5 to 50 parts by volume, and preferably 0.5 to 30 parts by volume of the preparation.

Being economical and easy to obtain, lecithin from egg yolks or soy beans may be used as the lecithin. Also, from the point of view of color and smell of the raw substance, a hydrogenated one is preferable, though an unhydrogenated type may of course be used. Further, commercially available synthesized lecithin (phosphatidyl choline) may be used. The amount of lecithin added is not particularly restricted, but should be in a ratio of 0.01 to 5 parts by weight, and preferably 0.02 to 2 parts by weight to 1 part by weight of azelastine hydrochloride.

The pH of the preparation according to the present invention should be adjusted to a physiological acceptable value of between 6 and 9. The pH of the preparation was measured by adding sufficient pure water to the preparation to form a 10% suspension. If the pH is lower than this, almost all of the azelastine is thought to exist in a state of dissociation, and is disadvantageous from the point of view of absorption of the drug. Also, depending on the type and amount of fatty acid to be incorporated and the composition of the preparation, there is sometimes precipitation of fatty acid or acid soap crystals, making it difficult to achieve the object of the present invention. If the pH is higher than this range, the ingredients incorporated in the preparation may be decomposed and there may be coloration of the preparation, making it unsuitable as a medicinal preparation.

Dosage forms of the preparation according to the present invention include liquid preparation such as eye drops, nasal drops, lotions, syrups and sprays, etc.; semi-solid preparations such as ointments, creams, gels, tapes and paps, etc.; and solid preparation such as suppositories. In addition to the above mentioned ingredients, these preparations may be made with other ingredients generally used as raw materials in medicinal preparations.

The ingredients used may, for example, be animal or vegetable oils (soy bean oil, beef tallow, synthesized glyceride, etc.), hydrocarbons (liquid paraffin, squalene, solid paraffin, etc.), ester oils (octyldodecyl myristate, isopropyl myristate, etc.), higher alcohols (cetostearyl alcohols, behenyl alcohols, etc.), silicon resins, silicon oils, surface active agents (polyoxyethylene fatty acid esters, sorbitan fatty acid esters, glycerine fatty acid esters, polyoxyethylenesorbitan fatty acid esters, polyoxyethylene hydrogenated castor oil, polyoxyethylene polyoxypropylene block copolymers, etc.), water soluble polymers (hydroxyethyl cellulose, polyacrylic acids, carboxyvinyl polymers, polyethylene glycols, polyvinyl pyrrolidone, methyl cellulose, etc.), alcohols (ethanol, isopropanol, etc.), polyhydric alcohols (glycerine, propylene glycol, dipropylene glycol, sorbitol, etc.), sugars (glucose, sucrose, etc.), inorganic powders (silicic acid anhydride, magnesium aluminum silicate, aluminum silicate, etc.), purified water, etc. For adjustment of the pH, inorganic acids (hydrochloric acid, phosphoric acid, etc.), alkali metal salts of inorganic acids (sodium phosphate, etc.), inorganic bases (sodium hydroxide, etc.), organic acids (lower fatty acids, citric acid, lactic acid, etc.), alkali metal salts of organic acids (sodium citrate, sodium lactate, etc.), organic bases (arginine, ethanolamine, etc.), etc. may be used. Also, if necessary preservatives, anti-oxidants, etc. may be added.

A preparation of the ingredients listed above may be produced according to any generally used method. An explanation will be given below of an example of a method for the production of a gel ointment. Azelastine hydrochloride, fatty acid and lecithin are measured out, and one or more ingredients selected from the group consisting of ethanol, isopropanol and polyhydric alcohols are added thereto, each ingredient is uniformly dissolved, and 0.1 N sodium hydroxide is added to prepare a solution. Separately, a Mitsuya Kako product called Carbopol (carboxyvinyl polymer) is dissolved, sodium hydroxide is used to adjust the pH of the gel to 8, and the pre-prepared solution is added thereto with adequate stirring to obtain a uniform gel ointment. According to the present invention, the mechanism of suppression of the production of azelastine hydrate is not clear. However, since such effect is not exhibited with the addition of acids having a small number of carbon atoms, such as acetic acid, propionic acid, butyric acid, etc, it is supposed that it is not due to a simple salt-exchange, but to a complicated interaction between each of the ingredients.

DETAILED DESCRIPTION OF PREFERRED EMBODIMENTS

A more detailed explanation will be made of the present invention with reference to examples given below, which should not be understood to be limitations thereto.

EXAMPLE 1 (Lotion)

0.3 g of azelastine hydrochloride, 0.28 g of myristic acid and 10 ml of ethanol were measured out, heated and dissolved. The resulting solution was added to purified water, and the pH was adjusted to 7.5 with sodium hydroxide to obtain a translucent lotion.

EXAMPLE 2 (Lotion)

0.3 g of azelastine hydrochloride, 0.28 g of myristic acid (Nippon Yushi Co.) and 0.1 g of lecithin (refined soy bean lecithin, Ajinomoto Co.) were weighed out, and 15 ml of ethanol was added thereto, and the mixture was heated to prepare a solution. The solution was added to purified water which contained 12 ml of 0.1 N sodium hydroxide, and ore purified water was added to make 100 ml. In this manner, a lotion having pH 8 and containing 0.3% azelastine hydrochloride was obtained

EXAMPLE 3 (Gel ointment)

0.3 g of azelastine hydrochloride, 0.5 g of oleic acid and 0.2 g of lecithin (PC-70, Nissin Seiyu Co.) were weighed out, 5 g of propylene glycol and 5 g of ethanol were added thereto and dissolved, and 9 g of 0.1 N sodium hydroxide was added to the solution. This was then added to 80 g of a gel containing 0.6 g of Carbopol 940 and purified water, and whose pH had been adjusted to 8 with sodium hydroxide, and adequate stirring was carried out for homogeneity. In this manner, a gel ointment having pH 8 and containing 0.3% azelastine hydrochloride was obtained.

EXAMPLE 4 (Cream)

3 g of stearic acid, 15 g of squalene SK®, 8 g of cetostearyl alcohol, 1 g of propylene glycol monostearate, 1 g of glycerine monostearate and 1 g of polyoxyethylenesorbitan monostearate (Nikkol TS-10, Nikko Chemicals Co.) were weighed out and heated to prepare a solution. Then 1.0 g of azelastine hydrochloride, 0.3 g of hydroxyethyl cellulose, 2 g of dipropylene glycol, 3 g of glycerine (Japanese Pharmacopeia), 1.7 g of disodium hydrogen phosphate, and an appropriate amount of water were weighed out and heated to prepare a solution. Both solutions were mixed and stirred, 11 ml of 0.1 N hydroxide was added thereto, and the mixture was cooled while stirring at room temperature. In this manner, a cream having pH 7.5 and containing 1% azelastine hydrochloride was obtained. The pH of the cream was measured as a 10% suspension in purified water.

EXAMPLE 5 (Ointment)

0.1 g of azelastine hydrochloride, 0.1 g lauric acid, 2 g of dipropylene glycol and 3 g of glycerine monooleate were weighed out and heated to prepare a solution. To this, there was added Plastibase 50W (Nippon Squibb Co.), and the mixture was adequately stirred. Then 0.45 ml of 1 N sodium hydroxide was further added thereto, and the mixture was well stirred for homogeneity, to obtain an ointment containing 0.1% azelastine hydrochloride. This ointment was mixed with water to form a 10% suspension, and after heating and stirring, the pH of the water phase was measured to be 7.5.

EXAMPLE 6 (Lotion)

0.3 g of azelastine hydrochloride and 0.3 g of oleic acid (Extra oleic 90, Nippon Yushi Co.) were weighed out, 16 ml of 0.05 N sodium hydroxide was added thereto, and the mixture was stirred and dissolved. To the resulting solution was added 5 g of propylene glycol and sufficient purified water was added to dilute to 100 ml and to form a lotion containing 0.3% azelastine hydrochloride.

EXAMPLE 7 (Eye drops)

0.05 g of azelastine hydrochloride, 1 g of propylene glycol and 0.05 g of myristic acid were weighed out and heated to prepare a solution. To the solution was added 1.37 ml of 0.1 N sodium hydroxide and then a solution of 1 g of glycerine, 0.1 g of methylparaben and 0.02 g of propylparaben in 80 ml of warm distilled water was added. After cooling, distilled water was added thereto to a total volume of 100 ml, and the solution was filtered with a 0.22 μm membrane filter to obtain an eye drop solution having pH 8 and containing 0.05% azelastine hydrochloride.

EXAMPLE 8 (Nasal drops)

0.01 g of azelastine hydrochloride, 0.01 g of lauric acid, 0.002 g of refined soy bean phospholipid, 1 ml of ethanol and 1 ml of glycerine were weighed out and heated to prepare a solution. Then 80 ml of purified water, 0.15 g of methylparaben and 0.2 g of hydroxyethyl cellulose were heated to prepare a solution, and 0.7 ml of 0.1 N sodium hydroxide was added thereto. Both solutions were mixed and stirred and purified water was added to a total volume of 100 ml to obtain a nasal drop solution having pH 7.5 and containing 0.01% azelastine hydrochloride.

EXAMPLE 9 (Syrup)

0.2 g of azelastine hydrochloride, 0.1 g of stearic acid, 0.1 g of myristic acid, 0.05 g of polysorbate 80, 0.5 g of ethanol, 3 g of glycerine and 6 ml of 0.1 N sodium hydroxide were weighed out and heated to prepare a solution. Then, 35 g of sucrose, 5 g of D-sorbit, 0.15 g of methylparaben, 0.05 g of propylparaben and an appropriate amount of fragrance were added thereto, and purified water was added to make 100 ml.

EXAMPLE 10 (Suppository)

0.5 g of azelastine hydrochloride, 0.8 g of lauric acid, 0.5 g of triethanolamine, 2 g of glycerine (Japanese Pharmacopeia) and 1.5 g of glycerine monooleate were weighed out and heated to prepare a solution, which was then added to 94.7 g of a melted suppository base (Witepsol H15R), mixed, poured into a suppository mold and cooled to obtain a suppository containing 0.5% azelastine hydrochloride.

EXPERIMENTS (AZELASTINE HYDRATE PRODUCTION-SUPPRESSING EFFECT OF EACH OF THE ADDITIVES)

[Experiment 1]

The azelastine hydrate production-suppressing effect was tested for each of the additives in azelastine hydro-chloride solutions. Each of the additives were added to 0.3 g of azelastine hydrochloride, the pH was adjusted to 8 with sodium hydroxide, and purified water was added to a total volume of 100 ml to determine whether or not azelastine hydrate crystals were produced. The identification of azelastine hydrate was carried out by filtering off the precipitates produced in the test solutions, drying them at room temperature, measuring thermal analysis (TG-DTA) (FIG. 1) and IR spectrum (azelastine hydrochloride reference standard: FIG. 2; azelastine hydrate: FIG. 3), and then comparing them to the standard.

Result

Table 1 shows the azelastine hydrate production-suppressing effect of each of the additives. Cases in which there was absolutely no hydrate formation are represented by [o], cases in which hydrate formation decreased compared to the produced water are represented by [Δ], and cases in which there was no hydrate production-suppressing effect are represented by [X]. It is clear from Table 1 that addition of fatty acids of 8 carbon atoms or greater had an azelastine hydrate production-suppressing effect.

TABLE 1

Azelastine Hydrate Production-Suppressing Effect of Each of the Additives

| Additive | Amount Added (%) | Effect Against Production of Azelastine Hydrates |
| --- | --- | --- |
| None | — | X |
| Propylene glycol | 30 | X |
| HCO-60 | 5 | X |
| Polyoxyethylene hydrogenated castor oil | 1 | X |
| Tween 80 | 5 | X |
| Ethanol | 30 | X |
| Acetic Acid | 0.5 | X |
| Propionic Acid | 0.3 | X |
| Butyric Acid | 0.5 | X |
| Caproic Acid | 0.5 | X |
| Caprylic Acid | 0.5 | Δ |
| Capric Acid | 0.5 | ○ |
| Lauric Acid | 0.5 | ○ |
| Myristic Acid | 0.1 | Δ |
| Myristic Acid | 0.3 | ○ |
| Myristic Acid | 0.5 | ○ |
| Palmitic Acid | 0.5 | ○ |
| Stearic Acid | 0.5 | ○ |
| Isostearic Acid | 0.5 | ○ |
| Behenic Acid | 0.5 | ○ |
| Palmitoleic Acid | 0.5 | ○ |
| Oleic Acid | 0.1 | Δ |
| Oleic Acid | 0.3 | ○ |
| Oleic Acid | 1.0 | ○ |
| Linolic Acid | 0.5 | ○ |
| Linolenic Acid | 0.5 | ○ |
| Erucid Acid | 0.5 | ○ |

[Experiment 2]

A small amount of the lotion in Example 1 was packaged into glass containers, and stored in a refrigerator, at room temperature or in an incubator at 45° C., and sequential observation was made for the presence or absence of azelastine hydrate. The result was that no azelastine hydrates were observed to be formed during 2 months under the test conditions.

[Experiment 3]

A percutaneous absorbability test was carried out for the preparations (Examples 1 and 5) according to the present invention.

[Method 3]

The abdomens of 8–11 week-old hairless rats (Ishikawa experimental animals) were shaved the day before the test with an electric clipper and shaver. On the day of the test, the skin was checked for cuts, the rats were sacrificed with an overdose of sodium pentobarbital, and the abdominal skin was excised. This was attached to a horizontal membrane type of percutaneous penetration experiment cell (effective penetration area 8.04 cm$^2$, receiver volume 46 ml) so that the epidermis was on the surface. The receiver used was an isotonic phosphate buffer solution at pH 7.4. To the donor side was added 1 ml of the preparation, the receiver solution was stirred on a water bath at 35° C. with a magnetic stirrer and sampling was made thereof at determined intervals. Then high performance liquid chromatography was used to measure the concentration of azelastine in the receiver solution in terms of azelastine hydrochloride.

(Comparison 1)

Purified water was added to 0.3 g of azelastine hydrochloride 100 ml. The pH of the solution at this time was 5.8.

(Comparison 2)

Purified water was added to 0.3 g of azelastine hydrochloride, adjusting the pH with sodium hydroxide, to make a total volume of 100 ml. The pH of the aqueous solution at this time was 8.0

Experimental Results

A quantitative determination was made of the azelastine in the receiver solution after 24 hours, and the amount of azelastine hydrochloride which had penetrated per 1 cm$^2$ of skin was expressed in μg. The results are shown in Table 2. It is clear from Table 2 that the preparation according to the present invention had the maximum percutaneous penetration of azelastine.

TABLE 2

Results of Percutaneous Absorbability Test

| | |
| --- | --- |
| Example 1 | 127 |
| Example 5 | 97 |
| Comparison 1 | 11 |
| Comparison 2 | 41 |

BRIEF DESCRIPTION OF THE DRAWINGS

In the drawings:

FIG. 1 shows a thermalanalysis (TG-DTA) diagram for azelastine hydrochloride and azelastine hydrate;

FIG. 2 shows an IR spectrum diagram for the azelastine hydrochloride reference standard; and FIG. 3 shows an IR spectrum diagram for azelastine hydrate.

What is claimed is:

1. A method for enhancing percutaneous absorbability of azelastine salt in a non-irritating composition comprising administering externally to a patient a non-irritating homogeneous pharmaceutical composition suitable for external use consisting essentially of a pharmacologically effective amount of an azelastine salt and a stabilizing amount of fatty acid selected from the group consisting of capric acid, lauric acid, myristic acid, palmitic acid, stearic acid, isostearic acid, behenic acid, oleic acid, palmitoleic acid, linolenic acid, erucic acid and linolic acid wherein fatty acid present is between a value more than 0.1 parts and 10 parts by weight of the azelastine salt, wherein the composition is free of the formation of azelastine hydrates.

2. The method as set forth in claim 1 in which the azelastine salt is azelastine hydrochloride.

3. The method as set forth in claim 2 in which the pharmacologically effective amount of azelastine hydrochloride is between 0.001 to 2% by weight of the composition.

4. The method as set forth in claim 3 in which the amount of said fatty acid is 0.3 to 10 parts by weight for each part by weight of azelastine hydrochloride.

5. The method as set forth in claim 4 in which the amount of said fatty acid is 0.5 to 5 parts by weight for each part by weight of azelastine hydrochloride.

6. The method as set forth in claim 2 wherein the composition has a pH of 6–9.

* * * * *